US00PP24873P3

(12) United States Plant Patent
Meilland

(10) Patent No.: US PP24,873 P3
(45) Date of Patent: Sep. 16, 2014

(54) GRANDIFLORA ROSE PLANT NAMED 'MEITAFNAH'

(50) Latin Name: *Rosa hybrida*
Varietal Denomination: Meitafnah

(71) Applicant: CP Delaware, Inc., Wilmington, DE (US)

(72) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 113 days.

(21) Appl. No.: 13/694,329

(22) Filed: Nov. 20, 2012

(65) Prior Publication Data

US 2014/0143915 P1 May 22, 2014

(51) Int. Cl.
*A01H 5/00* (2006.01)

(52) U.S. Cl.
USPC ..... Plt./137

(58) Field of Classification Search
USPC ..... Plt./137, 130, 138
See application file for complete search history.

*Primary Examiner* — Susan McCormick Ewoldt
(74) *Attorney, Agent, or Firm* — Buchanan, Ingersoll & Rooney, PC

(57) ABSTRACT

A new and distinct variety of Grandiflora rose plant is provided that abundantly and substantially continuously forms attractive double strongly fragrant blossoms that are violet pink in coloration. The vegetation is strong. An upright growth habit is displayed. The foliage is dense dark green with a semi-glossy upper surface. The disease resistance is good, with no particular disease concern having been encountered during observations to date. The plant is well suited for providing distinctive attractive ornamentation in the landscape.

1 Drawing Sheet

Botanical/commercial classification: *Rosa hybrida*/Grandiflora Rose Plant.

Varietal denomination: cv. Meitafnah.

SUMMARY OF THE INVENTION

The new variety of *Rosa hybrida* Grandiflora rose plant was created in France by artificial pollination wherein two parents were crossed which previously had been studied in the hope that they would contribute the desired characteristics. The female parent (i.e., the seed parent) was the product of the cross of the 'Meironsse' variety (U.S. Plant Pat. No. 8,496) and the 'Meipsilon' variety (non-patented in the United States). The male parent (i.e., pollen parent) was a non-patented unnamed and unreleased seedling.

The parentage of the new variety can be summarized as follows:

('Meironsse'×'Meipsilon')×Unnamed Seedling.

The seeds resulting from the above pollination were sown and small plants were obtained which were physically and biologically different from each other. Selective study resulted in the identification of a single plant of the new variety.

It was found that the new Grandiflora rose plant of the present invention:

(a) forms strong vegetation,
(b) exhibits an upright growth habit with dense dark green foliage having a semi-glossy upper surface,
(c) abundantly and substantially continuously forms attractive double strongly fragrant blossoms that display violet pink coloration, and
(d) is well suited for providing distinctive attractive ornamentation in the landscape.

The violet pink blossom coloration blends nicely with the semi-glossy dark green foliage.

The new variety well meets the needs of the horticultural industry and can be grown to advantage as colorful ornamentation in parks and gardens.

The new variety can be readily distinguished from its ancestors upon an inspection of the blossoms. More specifically, the 'Meironsse' variety forms Indian Orange edged with Capsicum Red blossoms and a semi-erect growth habit. The 'Meipsilon' variety forms dissimilar bicolored red and yellow blossoms.

The new variety also can be distinguished from other Grandiflora rose varieties. For instance, the blossoms of the new variety lack the heavily fruity fragrance of the 'Meisionver' variety (non-patented in the United States). When compared to the 'Meizincaro' variety (U.S. Plant Pat. No. 11,660), the 'Meizincaro' variety displays substantially more petals than the new variety.

The new variety has been found to undergo asexual propagation at Le Cannet des Maures, Var, France, by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meitafnah'.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately two years of age and were observed during June while asexually reproduced from cuttings and growing outdoors on their own roots at Le Cannet des Maures, Var, France. Standard color information is provided at the bottom of the photograph for comparative purposes.

DETAILED BOTANICAL DESCRIPTION

Figures 1, 2, 3, 4, 5, 6, 7, 8, 9, 10, 11, 12, 13, 14, 15:
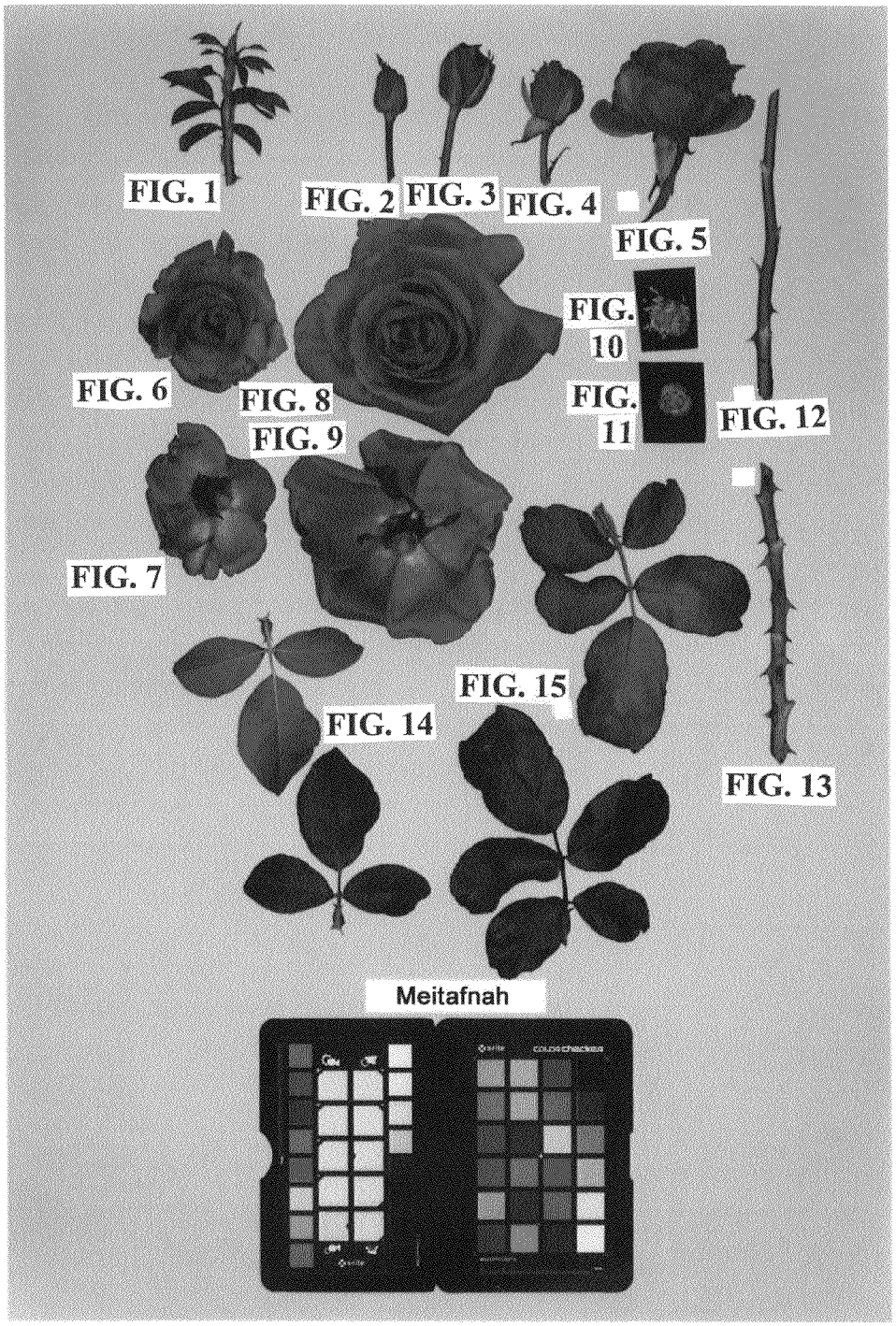
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing arrangement of the stamens and pistils.
FIG. 11 illustrates a specimen of a floral receptacle showing arrangement of the pistils (stamens removed)
FIG. 12 illustrates a specimen of a flowering stem.
FIG. 13 illustrates a specimen of a main branch.
FIG. 14 illustrates specimens of a leaf with 3 leaflets—plan view—upper surface (bottom) and—under surface (top)
FIG. 15 illustrates a specimen of a leaf with 5 leaflets—plan view—upper surface (bottom) and—under surface (top).

The chart used in the identification of the colors is that of The Royal Horticultural Society (R.H.S. Colour Chart—1995 or equivalent) except where ordinary color terms are utilized. Common color terms are to be accorded their customary dictionary significance. The description is based upon the observation of plants of the new variety at an age of approximately two years during the month of June while being grown outdoors on their own roots at Le Cannet des Maures, Var, France.

Class: Grandiflora.

Plant:

*Growth habit*.—Upright.

*Height*.—Commonly approximately 90 cm on average.

*Width*.—Commonly approximately 70 cm on average.

*Number*.—Commonly approximately four main branches on average.

Branches:

*Color*.—Young stems: commonly near Yellow-Green Group 146C. Adult wood: commonly near Yellow-Green Group 148A.

*Thorns*.—Configuration: curved downwards and elongated on the upper surface and concave on the under surface with an oval base. Quantity and size on young stems: commonly approximately 13 on average having a length of approximately 9 mm over a stem length of 10 cm. Quantity and size on adult stems: commonly approximately 19 on average having lengths of approximately 9 to 11 mm over a stem length of 10 cm. Color on young stems: near Yellow-Green Group 147C. Color on adult stems: near Greyed-Orange Group 174A.

Leaves:

*Overall appearance*.—Dense dark green.

*Leaflets*.—Shape: generally oval. Number: 3, and most often 5 and 7.

*Size*.—Terminal leaflets commonly are approximately 6.4 cm in length on average and approximately 4.5 cm in width on average. Apex: generally cuspidate. Base: obtuse. Serration: slightly denticulate, small and single. Texture: firm, and leathery, and semi-glossy on the upper surface. Color (young foliage): near Green Group 137C on the upper surface, and near Green Group 138B on the under surface. Color (adult foliage): near Green Group 139A on the upper surface, and Yellow-Green Group 148B on the under surface. Venation: regularly arranged around a main vein, and the coloration is Green Group 137C on the upper surface and near Yellow-Green Group 146B on the under surface.

*Petiole*.—Length: commonly approximately 3 cm on average. Texture: non-glandular on the upper surface and commonly with a few prickles on the under surface. Color: near Yellow-Green Group 146B on the upper surface, and near Yellow-Green Group 147C on the under surface.

*Rachis*.—Length: commonly near 1.7 cm on average. Diameter: commonly near 2 mm on average. Texture: smooth. Color: near Yellow-Green Group 152C on the upper surface, and near Yellow-Green Group 147C on the under surface.

*Stipules*.—General appearance: adnate, pectinate, and rather broad. Size: commonly approximately 1.9 to 2.2 cm in length on average, and approximately 6 mm in width on average. Color: near Yellow-Green Group 146C on the upper surface, and near Yellow-Green Group 146D on the under surface.

Inflorescence:

*Number of flowers*.—Commonly approximately 1 to 3 blossoms per stem.

*Buds*.—Shape: generally conical and medium in size. Length: approximately 2.3 cm on average. Width: approximately 1.7 cm at the widest point on average. Color: as the calyx breaks: on the upper surface near Red-Purple Group 57B and 57C edged and suffused with near Red-Purple Group 60C, and on the under surface near Red-Purple Group 57B and 57C edged and suffused with near Red-Purple Group 60C.

*Flower*.—Diameter: approximately 11 to 12 cm on average when fully open. Depth: approximately 7 cm on average. Shape: cup-shaped. Color (in course of opening): Upper side: near Red-Purple Group 57B and 57C edged and suffused with Red-Purple Group 60C with a spot of near Yellow Group 4B at the base. Under side: near Red-Purple Group 57B and 57C edged and suffused with Red-Purple Group 60C with a spot of near Yellow Group 4B at the base. Color (when open): Upper side: near Red-Purple Group 57D suffused with near Red-Purple Group 57B and 57C with a spot of near Yellow Group 4B at the base. Under side: near Red-Purple Group 61 C with a spot of near Yellow Group 4B at the base. Fragrance: strong. Petal number: commonly approximately 35 on average under normal growing conditions. Petal shape: commonly display a rounded tip and a rounded base. Petal arrangement: imbricated and commonly without petaloids. Petal texture: firm and leathery. Petal length: commonly approximately 4 cm on average. Petal width: commonly approximately 4 cm on average. Petal drop: good with the petals commonly detaching cleanly before drying. Stamen number: commonly approximately 72 on average. Anthers: arranged regularly around the styles, commonly approximately 2 mm in size on average, and near Yellow-Orange Group 22D in coloration. Filaments: commonly approximately 7 to 12 mm in length on average, and near Red Group 53D in coloration. Pistils: commonly approximately 49 on average. Styles: commonly approximately 2 mm in size on average, and near Yellow Group 4D in coloration. Stigmas: commonly approximately 1 mm in size and near Yellow-Orange Group 19D in coloration. Hips: conical in configuration, and commonly contain no seeds or up to six seeds.

Development:

*Vegetation*.—Strong.

*Blooming*.—Early season, very abundant and substantially continuous.

*Tolerance to diseases*.—Very good, with no particular disease concern having been encountered during observations to date.

I claim:

1. A new and distinct Grandiflora rose plant characterized by the following characteristics:

(a) forms strong vegetation, (b) exhibits an upright growth habit with dense dark green foliage having a semi-glossy upper surface, (c) abundantly and substantially continuously forms attractive double strongly fragrant blossoms that display violet pink coloration, and (d) is well suited for providing distinctive attractive ornamentation in the landscape;

substantially as shown and described.

* * * * *

Meitafnah